United States Patent [19]

Stuttle

[11] Patent Number: 5,843,402

[45] Date of Patent: *Dec. 1, 1998

[54] SYNTHETIC PEPTIDES FOR USE IN THROMBUS DETECTION

[75] Inventor: Alan William J. Stuttle, Hayes, United Kingdom

[73] Assignee: Antisoma Research Limited, London, United Kingdom

[*] Notice: The term of this patent shall not extend beyond the expiration date of Pat. No. 5,395,609.

[21] Appl. No.: 816,922

[22] Filed: Mar. 12, 1997

Related U.S. Application Data

[63] Continuation of Ser. No. 963,127, Oct. 19, 1992, abandoned, which is a continuation of Ser. No. 659,343, Mar. 21, 1991, abandoned.

[30] Foreign Application Priority Data

Jun. 19, 1989 [GB] United Kingdom ................... 8914020

[51] Int. Cl.[6] ........................... A61K 51/00; A61M 36/14
[52] U.S. Cl. ......................... 424/1.69; 530/331; 424/1.65
[58] Field of Search .................... 424/1.11, 1.65, 424/1.69, 9.1, 9.3, 9.4, 9.5; 530/300, 331

[56] References Cited

U.S. PATENT DOCUMENTS

| | | | |
|---|---|---|---|
| 4,427,646 | 1/1984 | Olexa et al. | 424/1.1 |
| 4,614,517 | 9/1986 | Ruoslahti et al. | 530/330 |
| 4,753,875 | 6/1988 | Ryan | 435/7.4 |
| 4,792,525 | 12/1988 | Ruoslahti et al. | |
| 4,986,979 | 1/1991 | Morgan, Jr. et al. | 424/1.53 |
| 5,100,875 | 3/1992 | Marguerie de Rotrou | 530/330 |
| 5,183,804 | 2/1993 | Saiki et al. | 530/327 X |
| 5,196,510 | 3/1993 | Rodwell et al. | 530/324 |
| 5,262,520 | 11/1993 | Plow et al. | 530/327 X |
| 5,279,812 | 1/1994 | Krstenansky et al. | 424/1.69 |
| 5,328,840 | 7/1994 | Coller | 530/300 X |
| 5,395,609 | 3/1995 | Stuttle | 424/1.69 |

FOREIGN PATENT DOCUMENTS

| | | |
|---|---|---|
| A-0063002 | 3/1982 | European Pat. Off. . |
| A-0205270 | 5/1986 | European Pat. Off. . |
| A-0333356 | 3/1989 | European Pat. Off. . |

OTHER PUBLICATIONS

Michael D. Pierschbacker, et al., Cell Attachment Activity of Fibronectin Can Be Duplicated By Small Synthetic Fragments of the Molecule, Nature, vol. 309, pp. 30–33, May 3, 1984.

G. E. Hanks, M.D., et al., The Outcome of Treatment of 313 Patents With T–I (UICC) Prostate Cancer Treated With External Beam Irradiation, Int'l. Radiation Onocology Biol. Phys., vol. 14, No. 2, pp. 243–248, Feb. 1988.

Marek Kloczewiak, et al., Platelet Receptor Recognition Domain on the τ Chain of Human Fibrinogen and Its Synthetic Peptide Analogues, Biochemistry, vol. 28, No. 7, pp. 2915–1919, 1989.

Marek Kloczewiak, et al., Platelet Receptor Recognition Site On Human Fibrinogen. Synthesis and Structure–Function Relationship of Peptides Corresponding to the Carboxy–Terminal Segment of the τ Chain, Biochemistry, vol. 23, pp. 1767–1774, 1984.

Jacek Hawiger, et al., Platelet Receptor Recognition Domains on the β Chain of Human Fibrinogen: Structure–Function Analysis, Biochemistry, vol. 28, pp. 2909–2914, 1989.

Burns et al., *J. Cell Biology*, vol. 107, pp. 1225–1230 (Sep. 1988).

Saiki et al., *Br. J. Cancer*, vol. 60, pp. 722–728 (1989).

D'Souza et al., *J. Biol Chem.*, vol. 263, No. 8, pp. 3943–3951 (Mar. 1988).

*Primary Examiner*—John Kight
*Assistant Examiner*—Dameron Jones
*Attorney, Agent, or Firm*—Banner & Witcoff, Ltd.

[57] ABSTRACT

Radioactively labelled peptides comprising oligopeptides of from 3 to 10 peptide units and containing the sequence RGD and particularly the oligopeptides RGDSY and RGDFY, are disclosed as in vivo thrombus, tumour or CAM markers for the in vivo diagnosis and detection or thrombi, tumours or CAM in mammals.

11 Claims, 1 Drawing Sheet

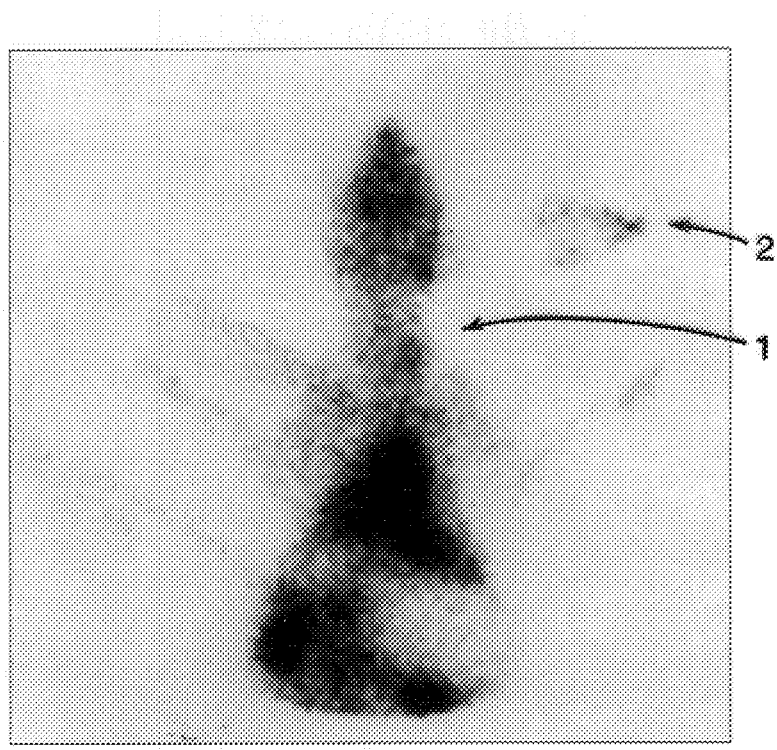

SYNTHETIC PEPTIDES FOR USE IN THROMBUS DETECTION

This is a continuation of application Ser. No. 07/963,127, filed Oct. 19, 1992, now abandoned, which, in turn, is a continuation of application Ser. No. 07/659,343, filed Mar. 21, 1991 now abandoned.

This invention relates, to the development and use of synthetic peptides for thrombus detection both in human beings and animals, but primarily, of course, in the detection of human disease. The method and the synthetic peptides used therein are also useful in targetting other sites *in vivo*, eg, cell adhesion molecules (CAMs) and tumors, containing an RGD binding site.

In 1984 Pierschbacher and Ruoslahti (Nature, 309, 30–33), showed evidence that the cell attachment activity of fibronectin could be mimicked by small synthetic peptide fragments. The amino acid sequence responsible for this activity was shown to be Arg-Gly-Asp-Ser (RGDS) and it was demonstrated that synthetic peptides containing this sequence were able to inhibit attachment of NRK cells (cells from a neuroblastoma cell line) to fibronectin coated substrates. The inhibition obtained with RGDS containing peptides was shown to be dose-related, while peptides which did not contain the RGDS sequence failed to inhibit cell attachment. The serine residue of the tetrapeptide has been shown to be nonessential, although only conservative substitutions may be made in order to retain biological activity.

The RGDS sequence has been shown to occur in fibrinogen, fibronectin and von Willebrand factor. Receptors for these proteins are expressed on the platelet membrane surface following platelet activation. Cross-linking of platelets via these cytoadhesive proteins accounts for the platelet-platelet interactions within a thrombus. It has also been demonstrated that RGDS containing synthetic peptides are capable of inhibiting platelet aggregation in vitro. This would suggest a specific interaction with the GP IIb/IIIa (glycoprotein fibrinogen receptor) complex present on the platelet membrane surface, which contains the fibrinogen binding domains. Extension of the RGDS sequence, by one amino acid residue at the carboxy and amino terminal, results in a ten-fold reduction in its biological activity, although further extension is not associated with a further reduction in binding capacity. Substitution of the serine residue by phenylalanine results in an anti-aggregatory peptide which is 4 to 5 times more potent than RGDS. There has also been suggestion that the residue corresponding to serine in the RGDS sequence may impart a degree of recognition specificity for different RGDS receptors. This raises the possibility that both specificity and affinity could be modified by substitution around the RGD sequence. RGD binding sites are also known to occur on cell adhesion molecules (CAMs) and some tumors.

The present Invention Involves a novel approach to *in vivo* thrombus detection and which comprises the intravenous injection into the patient (which term herein includes both humans and animals, unless the context requires otherwise) of a radioactively labelled synthetic peptide having therein an RGD (Arg-Gly-Asp)-containing sequence, preferably an RGDS (Arg-Gly-Asp-Ser) or RGDF (Arg-Gly-Asp-Phe)-containing sequence having a specific binding affinity for the platelet GP IIb/IIIa complex, and detecting the presence, if present, of the bound label on the thrombus. Present methods of thrombus detection using labelled antibodies require several hours due to the slow rate of diffusion of the antibody through the system; using labelled peptides in accordance with the present invention is expected to enable thrombus detection in a matter of minutes, thus greatly facilitating diagnosis and treatment, and at a very early stage.

For use in that method of *in vivo* thrombus detection there is provided in accordance with the present invention a synthetic peptide containing the sequence RGD, preferably as RGDS or RGDF, and labelled with a radioactive label.

Suitable radioactive labels for use in the construction of such radioactively labelled peptides include: $Tc^{99m}$, $I^{123}$ and $In^{111}$, and will be attached to the synthetic peptide in known manner, for example, via a cystine residue in the synthetic peptide. Other suitable techniques are described in Science, 220, 613–615; Int. J. Nucl. Med. Biol., 12, 3–8; J. Nucl. Med., 27, 27, 685–693 and J. Nucl. Med., 26, 293–299.

Subject to the dictates of suitability for parenteral administration and utility, i.e. high affinity and specificity for the GP IIb/IIIa complex, the precise amino acid sequence in terms of composition and length will not be particularly critical, although for practical reasons, e.g. economy and ease of synthesis, relatively short chain peptides will be preferred containing, for example, from 3 to 10 peptide units.

Suitable peptides containing an RGD sequence, preferably an RGDS or RGDF are available from a variety of different sources, or can be manufactured quite readily using conventional peptide synthesis procedures, and, in particular, using a conventional peptide synthesiser.

Also included within the scope of this invention are a diagnostic reagent for *in vivo* thrombus detection comprising a parenterally administrable solution of the radioactively labelled peptide containing an RGD sequence and a parenterally administrable carrier, and a method of *in vivo* thrombus detection which comprises intravenously administering a radioactively labelled peptide containing and RGD sequence capable of binding to RGD binding sites on platelets in the thrombus and radiographically detecting the accumulated bound peptide.

The invention also extends to the use of the radioactively labelled peptides in *in vivo* localisation on to the RGD binding sites of CAMs.

Before proceeding further with the detailed description of this invention, and for the avoidance of doubt, the amino acid sequences referred to herein are identified by either their three letter abbreviations or single letter codes, as follows:

arginine=arg. or R.
aspartic acid=asp. or D.
glycine=gly. or G.
serine=ser. or S
tyrosine=tyr. or Y
phenylalanine=phe. or F
cysteine=cys. or C Reference is also made hereinafter to the accompanying figure, which is a radiograph taken of a rabbit following intravenous administration of a radioactively labelled peptide according to this invention, and showing the localisation of the peptide in an artificially induced thrombus in the left ear.

Referring to the invention in slightly more detail, studies have been conducted using four peptides (RGDSY, RGDFY, RGDSYC and RGDSCRGDSY) to evaluate their potential as thrombus imaging agents.

The effect of these peptides on ADP-induced platelet aggregation was determined and compared with peptide RGDS which is known to inhibit platelet aggregation. The results (table 1) demonstrate that all four peptides studied are capable of inhibiting platelet aggregation at high concentrations and are virtually equipotent with RGDS. This suggests that inclusion of amino acids into these peptide sequences, to permit radio-labelling, does not destroy their ability to bind platelets (a prerequisite for thrombus imaging applications).

The second study involved radiodination of RGDSY, RGDFY, RGDSYC and RGDSCRGDSY with subsequent analysis of their ability to bind activated platelets in whole blood. The results (Table 2) indicate that all four peptides can bind platelets in ADP stimulated blood and that higher incorporation can be achieved In clotted blood.

One study was performed using RGDSY, labelled with the radioisotope iodine-123, injected into a rabbit who had a preformed thrombus in the microvasculature of the ear. The imaging studies, shown in the accompanying figure demonstrates a rapid uptake onto this thrombus (within 2 minutes of injection), which persisted for the period of study (20 minutes).

These data demonstrate that the four peptides studied are capable of binding to platelets, can be radiolabelled with gamma-emitting isotopes and are incorporated into platelet aggregates in stimulated and clotted blood. This provides good potential for thrombus detection and diagnosis by these peptides *in vivo* which has been confirmed, in an experimental animal model, using one of the peptides.

TABLE 1

Inhibition of ADP (1 × 10⁻⁵ M)-induced platelet aggregation by RGDS, RGDSY, RGDFY, RGDSYC and RGDSCRGDSY peptides.

| (peptide) | percentage inhibition | | | | |
|---|---|---|---|---|---|
| mM | RGDS | RGDSY | RGDFY | RGDSYC | RGDSCRGDSY |
| 0.1 | 40/37 | 5/13 | 32 | 25 | 17 |
| 0.2 | 70/65 | 10/21 | 55 | — | 57 |
| 0.4 | 86/80 | 43/68 | 80 | — | 79 |

TABLE 2

Binding of radiolabelled RGDSY, RGDFY, RGDSYC and RGDSCRGDSY peptides to ADP stimulated and clotted blood.

| (peptide) | (bound peptide) ng | | | |
|---|---|---|---|---|
| ng | RGDSY | RGDFY | RGDSYC | RGDSCRGDSY |
| ADP Stimulated blood | | | | |
| 1 | 0.05 | 0.01 | 0.03 | 0.01 |
| 10 | 0.64 | 1.00 | 0.94 | 0.85 |
| 100 | 9.80 | 4.46 | 9.85 | 9.07 |
| Clotted Blood | | | | |
| 1 | 0.27 | 0.41 | 0.18 | 0.28 |
| 10 | 0.85 | 2.14 | 2.26 | 2.64 |
| 100 | 17.27 | 18.12 | 27.08 | 29.33 |

The above results demonstrate the applicability of the invention over a synthetic peptides of different sizes all containing an RGD sequence. The actual length of the peptides is not critical, but for practical purposes the chain lengths may range from 3 to 10 peptide units, preferably 4 to 10 and, as already indicated, either consisting of or comprising an RGDS or RGDF sequence. Many such synthetic peptides are already available as known commercial products. Where not so available they can be readily synthesised by known peptide syntheses and/or using known peptide synthesisers. Similarly said synthetic peptides can be radioactively labelled by known techniques, for example, by iodination with $I^{123}$ of a terminal tyrosine (Y) unit incorporated into the peptide.

The detailed preparation of radioactively labelled peptides according to this invention is illustrated by the following example.

EXAMPLE

Preparation of radioactively labelled ($I^{123}$) RGDSY, RGDFY, RGDSYC and RGDSCRDSY Iodogen tubes were prepared by dissolving Iodogen (1, 3, 4, 6-Tetrachloro-3α, 6α-diphenylglycouril) in chloroform at a concentration of 1 mg.ml⁻¹. Aliquots of 50 µl (50 µg Iodogen) were dispensed into polypropylene cryo-tubes and the chloroform evaporated to dryness. These tubes were then stored dessicated at −20° C. until required.

Prior to radiolabelling the peptides were dissolved in phosphate buffered saline (PBS) at a concentration of 50 mg.ml⁻¹. RGDSYC and RGDSCRGDSY were first dissolved in a small volume of dimethyl sulphoxide (DMSO) such that the final concentration of DMSO in PBS was 1% v/v.

Iodogen tubes were equilibrated to room temperature before the addition of 200 µl peptide solution and 1–10 µl of $^{123}I$ (in aqueous solution). The reaction mixture was then left for 15min at room temperature with occasional shaking. Following the incubation period the reaction mixture was removed and passed through a Sephadex G10 column which had been equilibrated with PBS. The column, which separates radiolabelled peptide from free iodine was eluted with PBS and 2 ml fractions collected. Radioactivity in the fractions was measured and the eluted peptides, represented by the first radioactive peak from the column, collected and stored at 4° C. until required.

The utility of the radioactively labelled peptides in *in vivo* thrombus detection is illustrated by the following experiment.

EXPERIMENT

Intravenous administration of radioactively labelled ($I^{123}$) RGDSY to thrombitic rabbits A male New Zealand White rabbit (3 kg) was sedated by Intramuscular injection of Hypnorm (0.4 ml.kg⁻¹) and then anaesthetised by intravenous injection of Midazolam (2 mg.kg⁻¹).

Two permanent disc magnets were positioned externally in the region of the jugular vein and the rabbit was then injected with 0.2 g carbonyl iron microspheres suspended in 1 ml of contrast media (Omnipaque) via an artery of the left ear. This procedure causes microthrombi in the capillary beds of the ear, whilst iron particles passing through the ear are trapped by the magnetic field and induce thrombus formation in the jugular vein. $^{123}$I-RGDSY was injected intravenously into the contralateral ear 60 min after injection of iron. Dynamic imaging by gamma camera was performed using a 1 min frame rate for 20 min with the camera positioned anteriorly to include both ears, head and neck regions in the field of view.

Following intravenous administration of the labelled peptide, the rabbit was radiographed and the resulting radiograph is presented in the accompanying figure. As indicated by the radiograph, there was rapid uptake of the peptide by a thrombus in the jugular vein (arrow 1) and by multiple tiny thrombi in the left ear (arrow 2). The latter, in particular, demonstrates the possible utility of the invention in the detection of small thrombi *in vivo* and the possibility of early diagnosis and treatment.

I claim:

1. A method of in vivo detection of a thrombus in a patient which comprises the steps of intravenously administering to the patient a radioactively labelled peptide which binds in vivo to arginine-glycine-aspartic acid (RGD) binding sites on activated platelets on the thrombus, said peptide comprising the amino acid sequence arginine-glycine-aspartic acid (RGD) and an attached radioactive label, allowing for the labelled peptide to bind to the RGD binding sites on the activated platelets in the thrombus and for the unbound labelled peptide to clear systemically from the patient, and radiographically detecting the accumulated bound peptide.

2. The method according to claim 1, wherein the radioactively labelled peptide is labelled with a radioactive substance selected from the group consisting of $Tc^{99m}$, $I^{123}$ and $In^{111}$.

3. The method according to claim 1, wherein the radioactively labelled peptide comprises a peptide selected from the group consisting of the amino acid sequence arginine-glycine-aspartic acid-serine (RGDS) and the amino acid sequence arginine-glycine-aspartic acid-phenylalanine (RGDF).

4. The method according to claim 1, wherein the radioactively labelled peptide is selected from the group of peptides consisting of RGDSY, RGDFY, RGDSYC and RGDSCRGDSY, to which a radioactively labelled has been attached.

5. The method according to claim 1, wherein the radioactively labelled peptide is a relatively short chain peptide.

6. The method according to claim 1, wherein the radioactively labelled peptide has from 3–10 amino acid units.

7. The method according to claim 1, wherein the radioactively labelled peptide is a synthetic peptide.

8. A diagnostic reagent for the in vivo localization and subsequent imaging of a thrombus having arginine-glycine-aspartic acid (RGD) binding sites, said diagnostic agent comprising a peptide having an the amino acid sequence arginine-glycine-aspartic acid (RGD) and an attached radioactive label in admixture with a parenterally administrable carrier.

9. A diagnostic reagent according to claim 8, wherein the radioactive label is selected from the group consisting of $Tc^{99m}$, $I^{123}$ and $In^{111}$.

10. A diagnostic reagent according to claim 8, wherein the peptide is a synthetic peptide.

11. A diagnostic reagent according to claim 8, wherein the diagnostic agent is selected from the group of peptides consisting of RGDSY, RGDFY, RGDSYC and RGDSCRGDSY, to which a radioactive label has been attached.

* * * * *

UNITED STATES PATENT AND TRADEMARK OFFICE
CERTIFICATE OF CORRECTION

PATENT NO. : 5,843,402
DATED : March 12, 1997
INVENTOR(S) : Stuttle, Alan J.

It is certified that error appears in the above-identified patent and that said Letters Patent is hereby corrected as shown below:

On the Cover Page; Section [63] should read as follows:

Related U.S. Application Data-Continuation of Ser. No. 963,127, Oct. 19, 1992, abandoned, which is a continuation of Ser. No. 659,343, Mar. 21, 1991, abandoned, which is a 35 U.S.C. 371 filing of PCT/GB90/00933, June 18, 1990.

Signed and Sealed this

Twelfth Day of September, 2000

Attest:

Q. TODD DICKINSON

Attesting Officer

Director of Patents and Trademarks